United States Patent [19]
Adair

[11] Patent Number: 5,817,015
[45] Date of Patent: *Oct. 6, 1998

[54] ENDOSCOPE WITH REUSABLE CORE AND DISPOSABLE SHEATH WITH PASSAGEWAYS

[76] Inventor: Edwin L. Adair, 317 Paragon Way, Castle Pines Village, Colo. 80104

[*] Notice: The term of this patent shall not extend beyond the expiration date of Pat. No. 5,704,892.

[21] Appl. No.: 909,721

[22] Filed: Aug. 12, 1997

Related U.S. Application Data

[63] Continuation-in-part of Ser. No. 375,934, Mar. 15, 1996, Pat. No. 5,704,892, which is a continuation-in-part of Ser. No. 80,323, Jun. 22, 1993, Pat. No. 5,402,323.

[51] Int. Cl.$^6$ .................................................. A61B 1/04
[52] U.S. Cl. ........................ 600/121; 600/182; 600/439
[58] Field of Search .............................. 600/121, 123, 600/125, 171, 172, 173, 175, 176, 182, 177, 162, 109, 104, 437, 439, 459, 462; 604/263

[56] References Cited

U.S. PATENT DOCUMENTS

| | | | |
|---|---|---|---|
| 3,581,738 | 6/1971 | Moore | 128/6 |
| 3,866,599 | 2/1975 | Johnson | 128/6 |
| 4,349,032 | 9/1982 | Koyata | 600/139 |
| 4,646,722 | 3/1987 | Silverstein et al. | 128/6 |
| 4,765,313 | 8/1988 | Kumakura | 128/6 |
| 4,854,302 | 8/1989 | Allred, III | 128/6 |
| 4,856,495 | 8/1989 | Tohjoh et al. | 128/6 |
| 4,878,485 | 11/1989 | Adair | 128/6 |
| 4,919,112 | 4/1990 | Siegmund | 128/4 |
| 5,201,908 | 4/1993 | Jones | 128/4 |
| 5,207,684 | 5/1993 | Nobles | 606/108 |
| 5,222,477 | 6/1993 | Lia | 128/6 |
| 5,237,984 | 8/1993 | Williams, III et al. | 128/4 |
| 5,257,617 | 11/1993 | Takahashi | 128/4 |
| 5,573,493 | 11/1996 | Sauer et al. | 600/121 |
| 5,704,892 | 1/1998 | Adair | 600/121 |

FOREIGN PATENT DOCUMENTS

| | | | |
|---|---|---|---|
| 3508833 | 9/1986 | Germany | 128/4 |

Primary Examiner—Beverly M. Flanagan
Attorney, Agent, or Firm—Fields and Johnson, P.C.

[57] ABSTRACT

An endoscope in one configuration includes an elongated cylindrical core with a transparent window at the distal end thereof. A removable housing is placed within the core along with an objective endoscope lens or optics at the distal end thereof. A photosensitive image sensor is mounted within the core. A transmitting electronic means with multiple conductors each has a distal end connected to the image sensor circuit board or image sensor and a proximal end connected to a video control unit. From the video control unit signals are transmitted to the video monitor which displays the image. A separable and disposable sheath or channel section is provided in a sterile condition and removably receives the core in a defined relationship. The sheath has at least one longitudinal channel formed around its periphery for transmitting fluids or for receiving an operative instrument or carrying light transmitting fibers. A flexible tube is connected to the proximal end of the sheath for supplying fluid or for manipulating the operative instrument from a remote location. The sheath is disposable after use on a patient and the core is prepared for reuse with another sheath on the next patient. In a second configuration, an ultrasound transducer is placed through the core after a first visual image of the desired area has been taken by the image sensor. The core is open at the distal end to permit the transducer to extend beyond it during use.

7 Claims, 6 Drawing Sheets

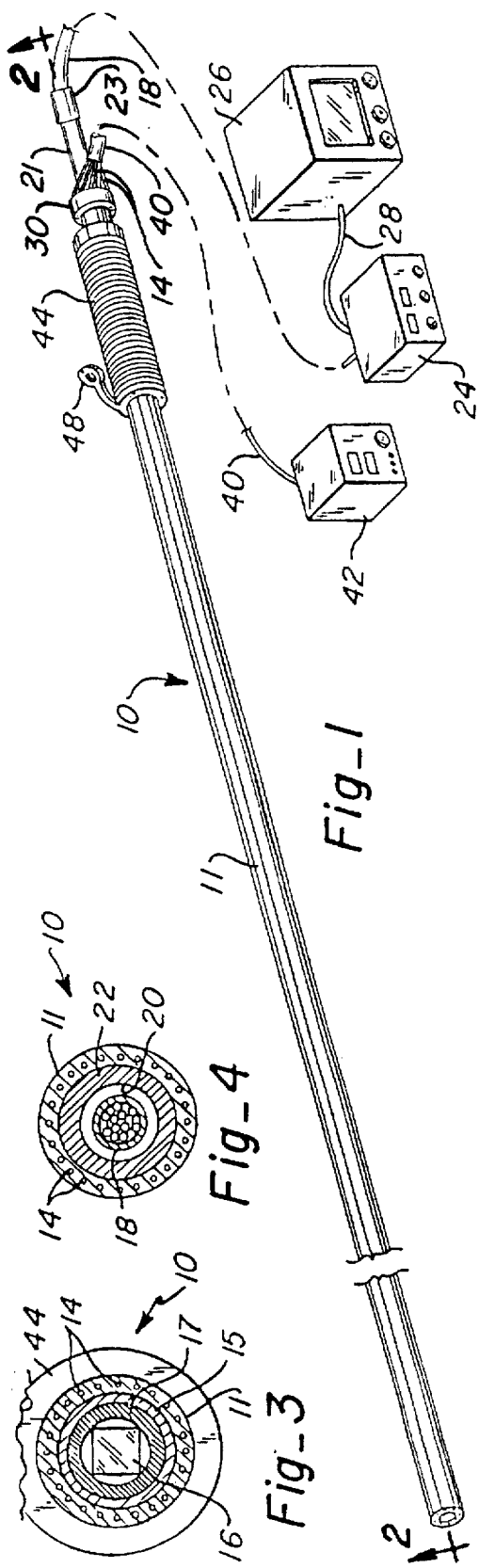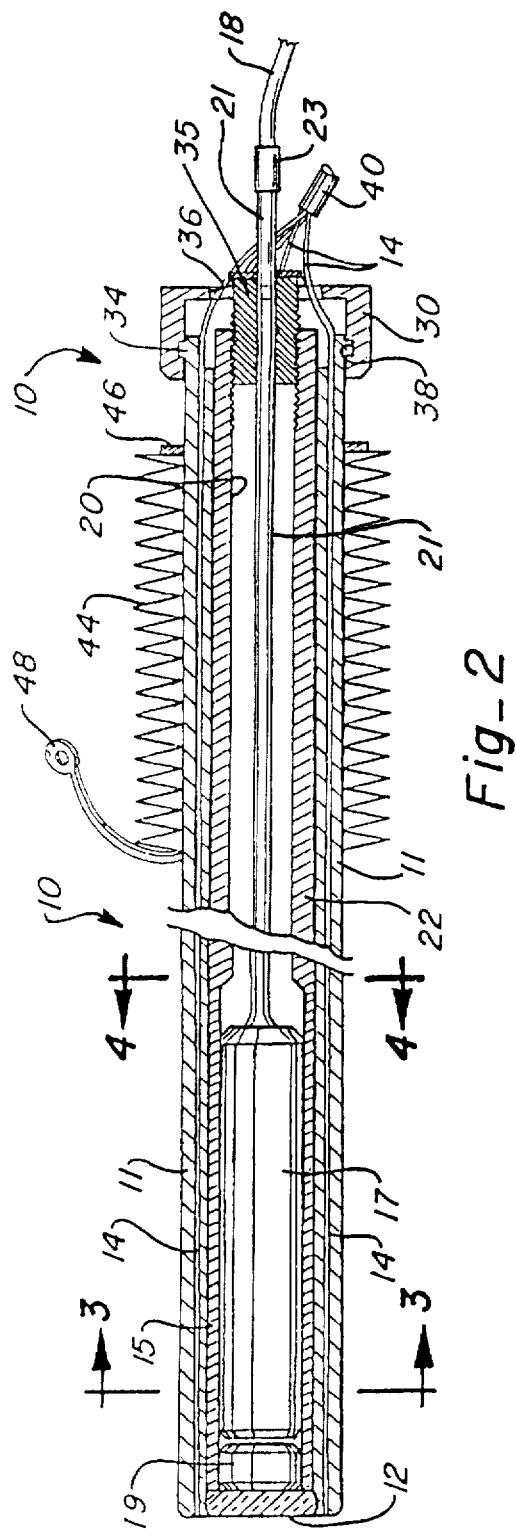

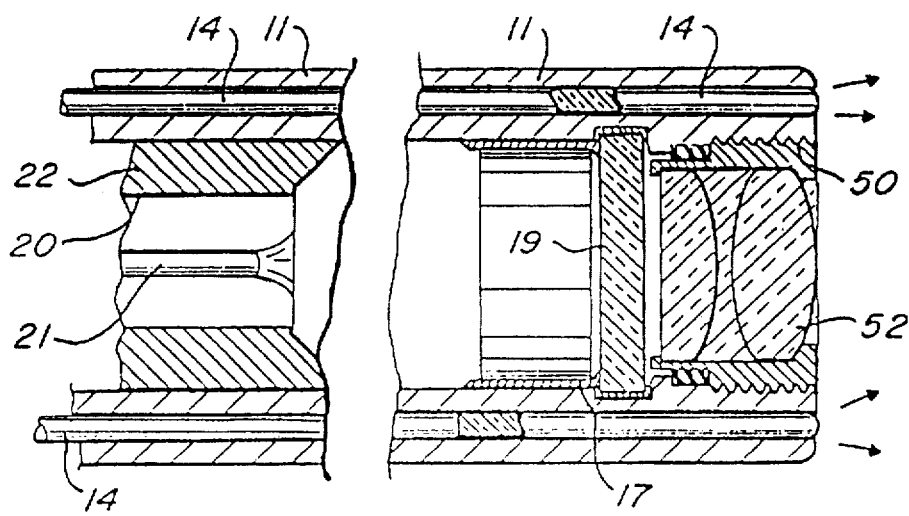
Fig_5
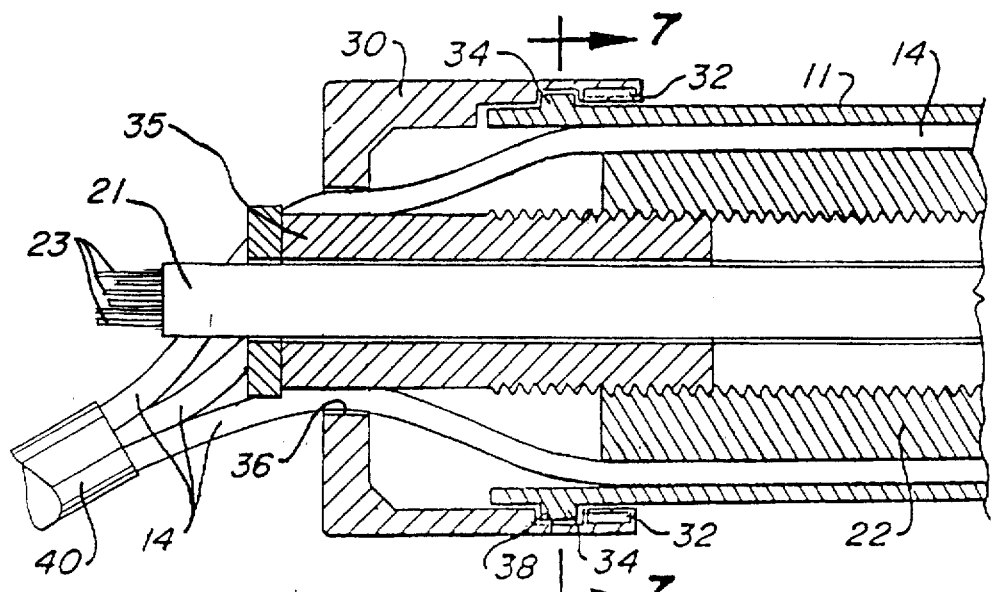
Fig_6
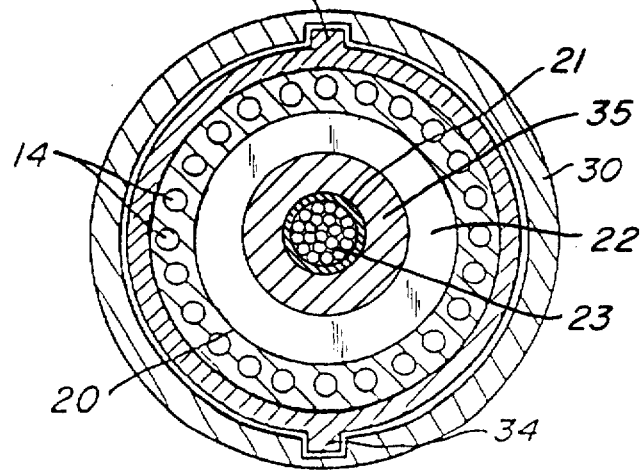
Fig_7

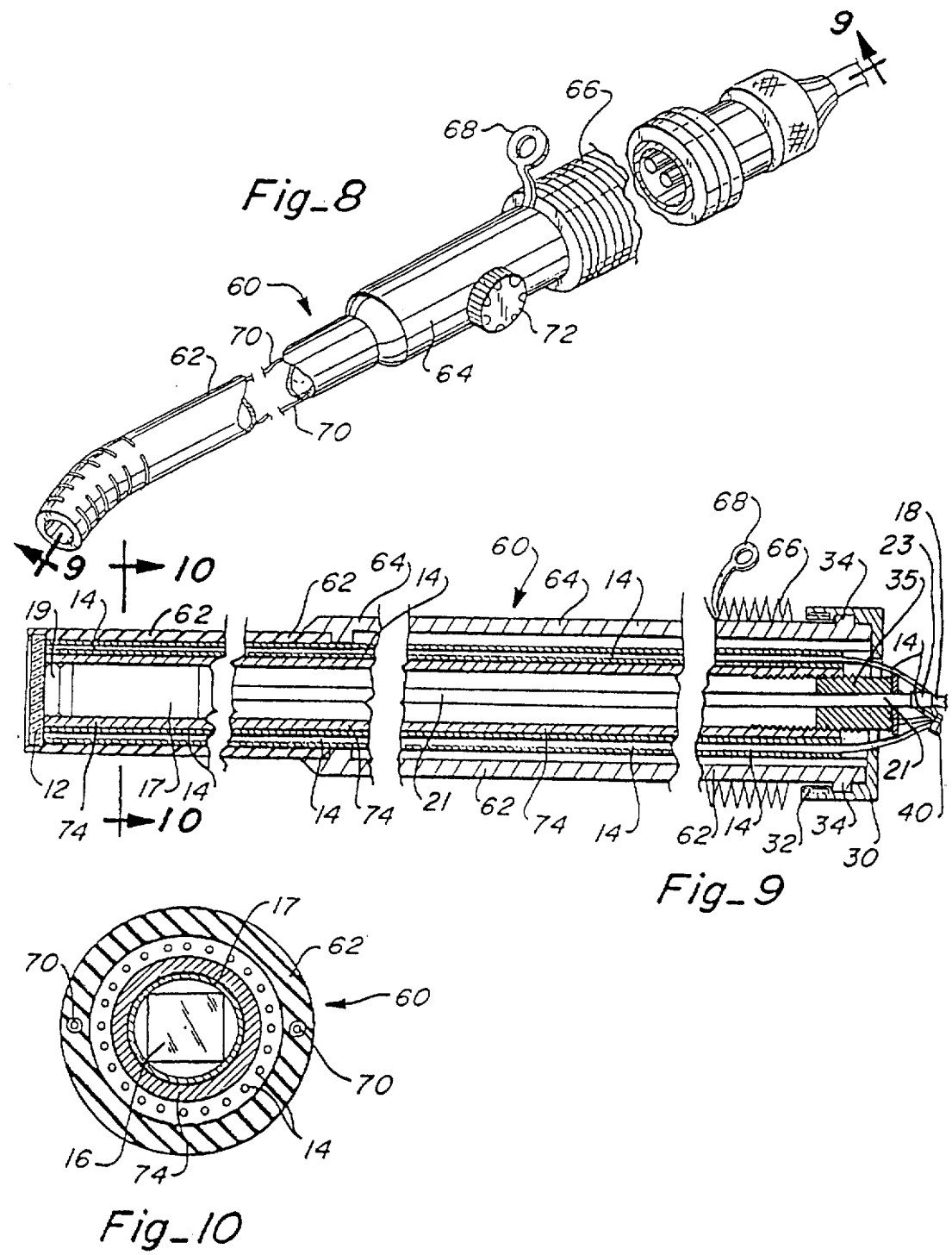

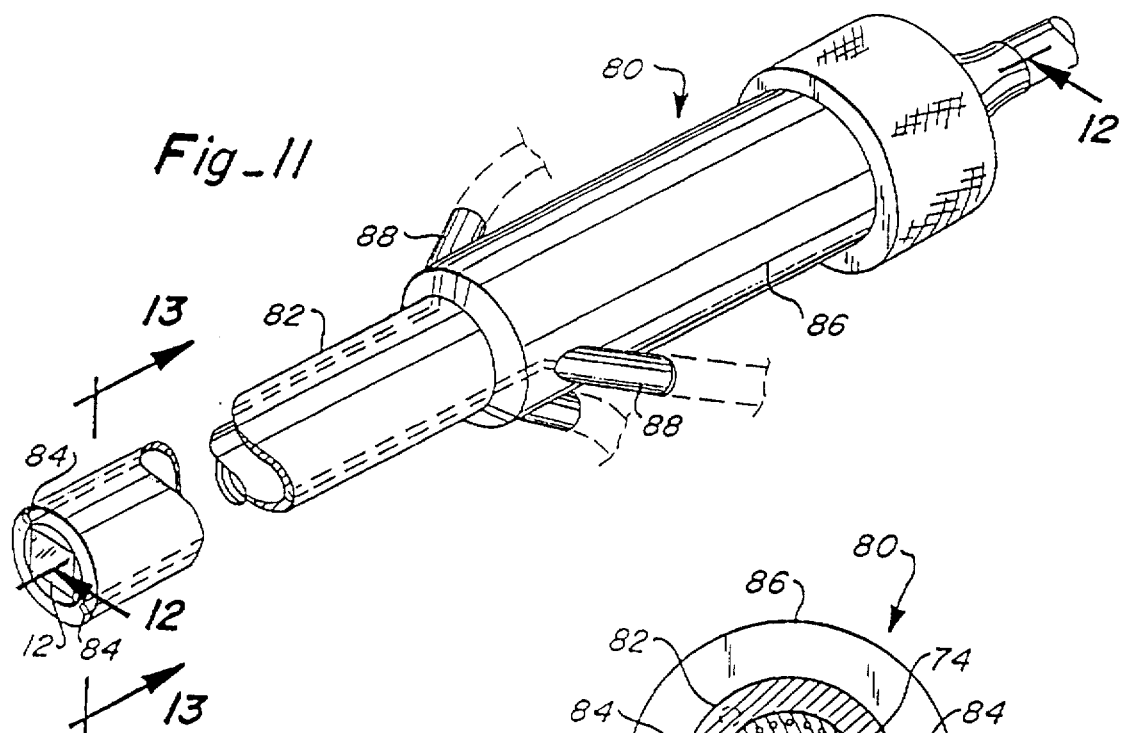
Fig_11
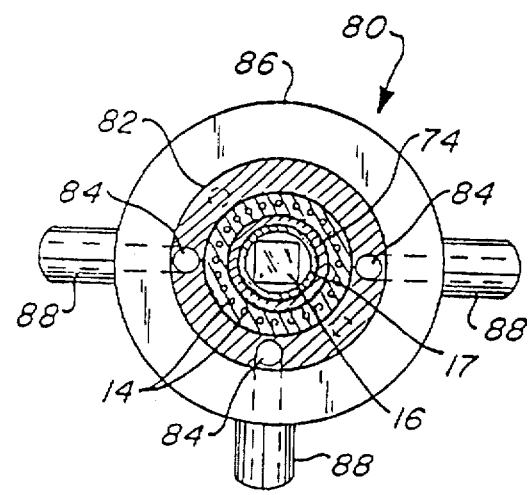
Fig_13
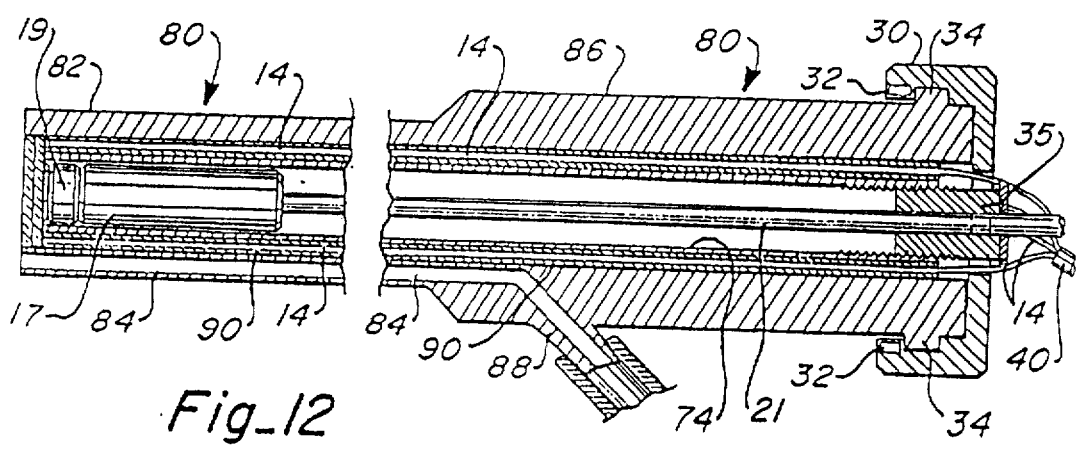
Fig_12

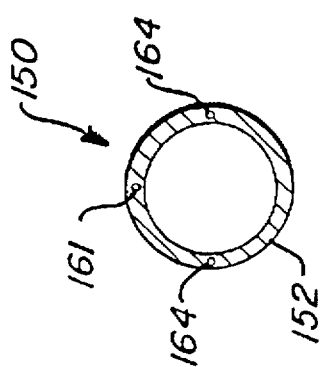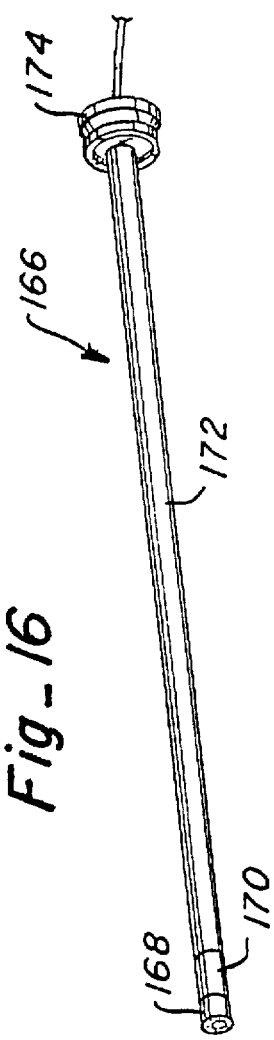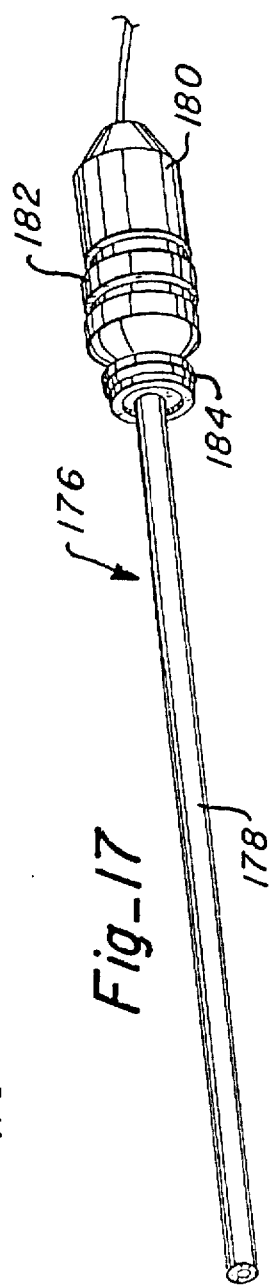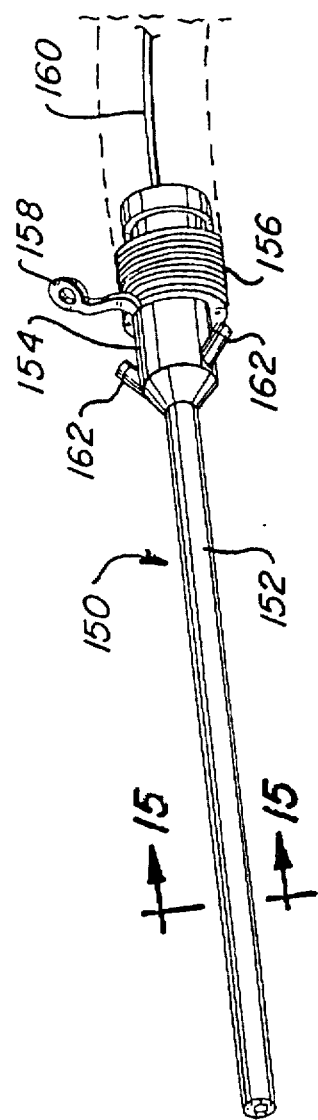

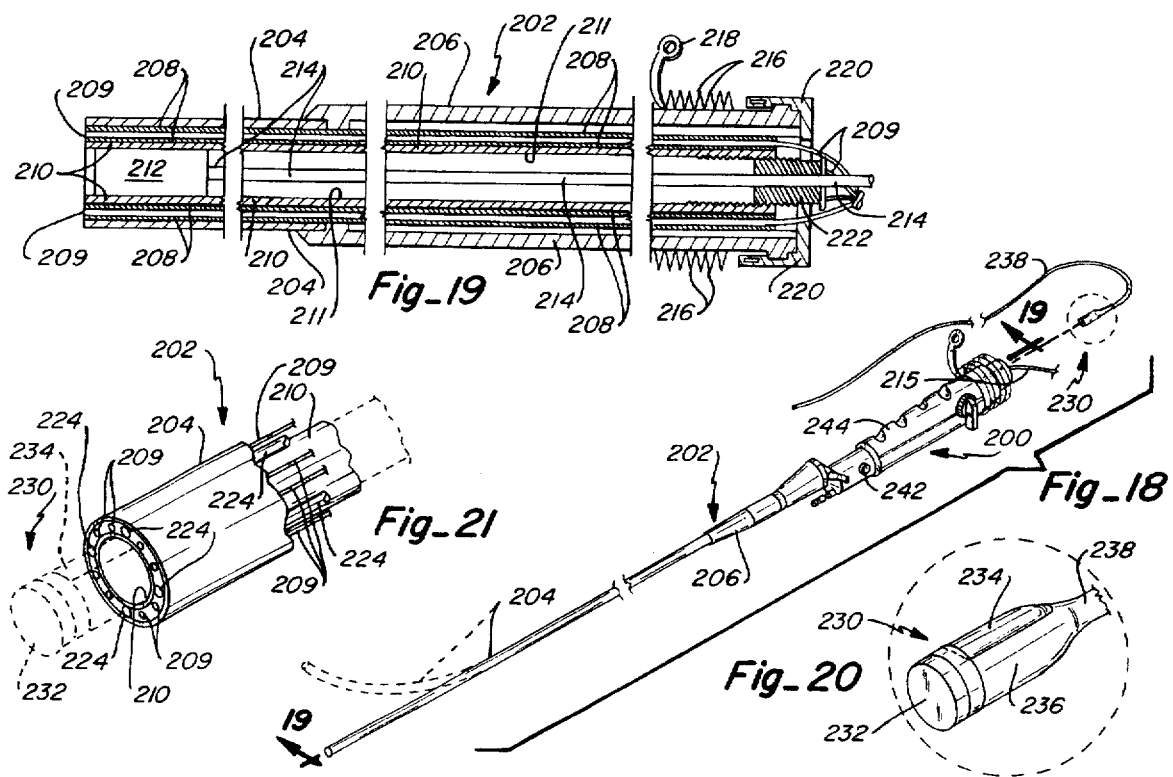

ENDOSCOPE WITH REUSABLE CORE AND DISPOSABLE SHEATH WITH PASSAGEWAYS

This Application is a continuation-in-part of U.S. application Ser. No. 08/375,934, filed Mar. 15, 1996 and entitled "Endoscope With Reusable Core and Disposable Sheath With Passageways", now U.S. Pat. No. 5,704,892, which is a continuation-in-part of U.S. application Ser. No. 08/080,323, filed Jun. 22, 1993 which is now U.S. Pat. No. 5,402,768.

TECHNICAL FIELD

This invention relates to an endoscope, and more particularly to an endoscope with a separable and disposable, initially sterile outer sheath containing one or more passageways, and a reusable inner core which contains optics, an image sensor and electronics.

BACKGROUND ART

In recent years the popularity of endoscopic surgery has proliferated. This has occurred because of the advances in technology which allow smaller and smaller endoscopes to be used, thereby permitting operative procedures to be undertaken in a less invasive manner for the patient than was previously possible. Thus, the patient suffers less trauma, recuperates much more rapidly, and experiences less pain and discomfort than with more conventional surgical procedures.

Because of the sophisticated optics and electro-optics contained in modern endoscopes, they generally are very expensive. In order for this expense to be justified, they must be reused with a large number of patients.

Of course, multiple use means that the endoscope must be sterilized after use with each patient prior to use with the next patient. One protocol for pre-operative preparation involves immersing the endoscope in a disinfectant solution for a predetermined period of time. It is also important to flush the channels which carry gases or fluids and those channels which are used for receiving operative instruments. Another protocol is to heat sterilize the endoscope by placing it in an autoclave. However, the optics and electronics of many endoscopes will not permit them to be subjected to heat sterilization. When using the disinfectant, the endoscope may not be placed in the disinfecting solution for a sufficient length of time or the channels may not be properly flushed out. Over time, the disinfectant solution may loose some of its strength, thereby limiting its effectiveness.

Because of these shortcomings, many studies show that transmission of infectious diseases from one patient to another has occurred. By way of example, transmission of salmonella typhi has been reported. In addition, pseudomonas aeruginosa cross infection has been linked to endoscopy. Also, an outbreak of serratia marcescens has been associated with the use of a bronchoscope. Furthermore, hepatitis B has been transmitted by endoscopes when the endoscopes were processed in an inappropriate manner between patients. Finally, with respect to endoscopes used on AID's patients it has been found that the sterilizing procedures have not always removed contamination of the human immunodeficiency virus (HIV). This list is not exhaustive by any means.

A high level of disinfection failures among gastrointestinal endoscopes has been noted, as well as failures in bronchoscopes, laryngoscopes and other devices. This may be due to the fact that they are long and narrow and have channels which are difficult to properly inspect, disinfect and sterilize.

From the foregoing, it is apparent that endoscopes are needed which can be more easily and effectively sterilized.

In addition to the shortcomings of prior art endoscopes with respect to sterility, most endoscopes are limited in their ability to introduce standard surgical instruments to the surgical area. This is so because the operative channels which are attached to or integral with the endoscope for purposes of introducing the surgical instrument along side the endoscope must be made small enough so that the overall endoscope diameter is not too large. Most standard surgical instruments cannot be placed through the small operative channels and special operative instruments must be used in lieu thereof. Often times these special operative instruments are not capable of carrying out a particular procedure as efficiently as standard surgical instruments. The size of the endoscope is always a major factor in determining patient trauma. Typically, the smaller the endoscope, the less trauma the patient will experience. Thus, large operative channels formed along side or integral with the endoscope create a problem.

Therefore, it is apparent that endoscopes are needed which may be small in size, yet may also accommodate surgical instruments to be introduced through the endoscopic instrument. Particularly in circumstances when ultrasound imaging is desired, the use of trochar entry sites makes it particularly difficult to place the ultrasound transducer in the right location. That is, there is no means by which the transducer can be stabilized in an exact location within the body of the patient by use of a trochar entry. Additionally, most transducers are too large to be placed through an operative channel of the endoscope. Therefore, the introduction of a transducer with the endoscope is not possible because of the resulting large size of the endoscope.

DISCLOSURE OF THE INVENTION

In accordance with the present invention, an improved endoscope in one configuration has been provided which includes an elongated cylindrical core having mounted thereon a housing containing an image sensor. An objective lens may also be mounted within the core and placed distally of the housing containing the image sensor. The image sensor and its associated electronics, e.g., a circuit board, is slidably mounted adjacent the objective lens within the housing. The image sensor may be a CCD, CMOS, or other type well known in the art. Multiple conductors each have a distal end connected to the image sensor electronics and a proximal end connected to a video control unit. From the video control unit signals are transmitted to a video monitor which displays the image in black and white or color. A separable outer cylindrical sheath, which is provided in a sterile condition, removably receives the core in a defined relationship and the sheath has at least one longitudinal channel for transmitting fluids or for receiving an operative instrument or carrying a light transmitting fiber. Once the housing has been placed within the core, the housing may be freely rotated within the core or may be moved longitudinally within the core at very precise increments. The rotation of the housing allows images processed by the image sensor to be viewed at the desired angle or orientation. The longitudinal movement of the housing within the core enables the images to be better focused or otherwise manipulated based upon the type of the optic lens used. The rotational movement and longitudinal movement of the housing may be achieved independently or simultaneously with one another. The sheath may further include a window or optically clear cap sealed at the distal end thereof. The window or cap isolates the core within the sheath yet allows the surgical area to be viewed by the image sensor.

A flexible or rigid supply tube is connected to the proximal end of the channel for supplying fluid or for manipulating the operative instrument from a remote location. The separable sheath is disposable after use on a patient and the core is prepared for reuse with another sterile sheath on the next patient. Light transmitting fibers can be integral with the core or inserted in one or more of the channels in the sheath.

Optionally, a connection may be provided at the distal end of the sheath or core for selective mounting of lens or filter attachments which may provide straight ahead or angled fields of view. This selection of lenses are mounted either inside or outside of the sealed terminal window of the device. The externally or outside mounted lenses or filters may be heat sterilized.

In addition, the transmitting electronic cable with multiple conductors may be housed within a rigid tube or rod which extends from the housing proximally through the core and may extend far enough to exit the core. A flexible cable may connect to the rigid tube or rod and house the transmitting electronic cable as it further extends away from the core. Conveniently, the rigid rod or tube may be stabilized with respect to the core by means of a connecting means which releasably interconnects the proximal end of the rigid rod or tube to the proximal end of the core. This connection may be accomplished by a plurality of threads formed on the connecting means and proximal end of the sheath, or by a bayonet attachment or by other means known by those skilled in the art. The connecting means may be in the form of a focusing member which also serves to move the housing longitudinally within the core. Furthermore, an end cap may be used to stabilize the connecting means with respect to the sheath, or otherwise provide structure by which the connecting means maintains a desired spacial relationship with the sheath.

In another embodiment, the distal end of the endoscope may be left open so that after an image of the surgical area has been made, another instrument such as a transducer may be inserted through the housing. This arrangement is particularly advantageous for introducing a transducer used in ultrasound imaging.

BRIEF DESCRIPTION OF THE DRAWINGS

FIG. 1 is a perspective view of an endoscope having a reusable core within a throwaway or disposable sheath;

FIG. 2 is an enlarged, fragmentary, longitudinal section, taken along line 2—2 of FIG. 1, showing additional details of the core and sheath;

FIG. 3 is a transverse section, taken along line 3—3 of FIG. 2, showing additional details of the core and sheath;

FIG. 4 is a transverse section, taken along line 4—4 of FIG. 2, showing still further details of the core and sheath;

FIG. 5 is an enlarged, fragmentary, longitudinal section of an endoscope showing a removable lens assembly;

FIG. 6 is an enlarged, fragmentary, longitudinal section showing an end cap and a focusing member;

FIG. 7 is a transverse section, taken along line 7—7 of FIG. 6, showing further details of the end cap;

FIG. 8 is a fragmentary perspective view of an alternative endoscope embodiment having steering means;

FIG. 9 is an enlarged, fragmentary, longitudinal section, taken along line 9—9 of FIG. 8, showing further details of the endoscope;

FIG. 10 is a transverse section, taken along line 10—10 of FIG. 9, showing additional details of the endoscope;

FIG. 11 is a fragmentary, perspective view of a further alternative embodiment having operative channels in the sheath;

FIG. 12 is a fragmentary, longitudinal section, taken along line 12—12 of FIG. 11, showing further details of the endoscope;

FIG. 13 is a transverse section, taken along line 13—13 of FIG. 11, showing additional details of the endoscope;

FIG. 14 is a perspective view of a still further embodiment of a disposable sheath forming a part of an endoscope;

FIG. 15 is an enlarged transverse section, taken along line 15—15 of FIG. 14, showing details of the construction of the sheath;

FIG. 16 shows one form of a core for use with the sheath of FIG. 14;

FIG. 17 shows a second form of a core for use with the sheath of FIG. 14;

FIG. 18 is a perspective view of yet another alternative endoscope embodiment including a steerable distal end which is left open so that a transducer may be inserted through the housing after a visual image of the surgical area has occurred;

FIG. 19 is an enlarged, fragmentary, longitudinal section, taken along line 19—19 of FIG. 18, showing further details of this particular embodiment;

FIG. 20 is a greatly enlarged, fragmentary, perspective view of one type of transducer which may be introduced through the endoscope of this embodiment; and FIG. 21 is a greatly enlarged, fragmentary, perspective view of the distal end of the endoscope of this embodiment illustrating the transducer of FIG. 20 inserted through the endoscope and beyond the distal end thereof.

BEST MODE FOR CARRYING OUT THE INVENTION

One form of the endoscope 10 of the present invention is shown in FIGS. 1–7 wherein a throwaway channel section in the form of a cylindrical sheath 11 has a window 12 at its distal end. A plurality of peripherally spaced longitudinal channels are provided in the side wall of sheath 11 for receiving light fibers 14, as shown, or operative instruments, fluid or gas. A cylindrical core 15 is removable and receivable within sheath 11. An image sensor 16 is slidably mounted within a housing 17 which contains the electronics for the image sensor. An objective lens 19 is hermetically sealed in the distal end of core 15 enabling delivery of an image to image sensor 16. Rigid tube or rod 21 extends from the proximal end of housing 17 for propagating the electronic signals to a video control unit (not shown). Tube or rod 21 houses the conductors 22 (FIG. 7) as they extend from the image sensor 16 and within the core 15. Rod 21 extends through a passageway 20 in end portion 22 formed at the proximal end of core 15, as best seen in FIG. 2. Housing 17 is movable longitudinally by focusing member 35 which is fixedly attached to rod 21 and threadably attached to end portion 22 of core 15. By turning focusing member 35, rod 21 causes housing 17 to be movable either closer to or farther away from objective lens 19. This in-and-out capability allows separation of the image sensor 16 from the objective lens 19 and thereby provides for focusing of an image at the operative site on the image sensor.

Rod 21 may terminate adjacent focusing member 35, or may extend as far as necessary to shield the conductors 22. In most circumstances, it will be desirable to further shield conductors 22 by means of a flexible cable 18 which may attach directly to rod 21 by means of fitting 23. Flexible cable 18 may be constructed of any well-known material which houses electronic cables or conductors. As shown in FIG. 1, flexible cable 18 connects to a camera control unit 24 which in turn is connected to a video monitor 26 by means of a cable 28. Housing 17 may be rotated within core 15 by rotating the exposed end of tube 21 or fitting 23. Twisting the tube or fitting in this manner causes the housing 17 to be rotated in the desired direction since tube 21 is rigid and fixedly attaches to housing 17. Accordingly, the opening in focusing member 35 through which tube or rod 21 extends is of a size large enough to allow rotation of the rod or tube yet provides enough support to rod or tube 21 such that housing 17 remains in its rotated position after manipulation. The rotation of housing 17 within core 15 may be accomplished independent of the manipulation of focusing member 35 such that only the orientation or angle of the image is altered and not the focusing distance of the image sensor with respect to objective lens 19. Similarly, the orientation or angle at which an image is viewed by maintaining the housing 17 at a steady position within core 15 can be maintained while the focusing distance between objective lens 19 and the image sensor 16 within housing 17 is altered. This can be accomplished by holding fitting 23 or the exposed end of rigid tube 21 and then rotating focusing member 35 without also rotating housing 17. An end cap 30 has a pair of slots 32 which align with a pair of oppositely spaced tabs 34 on the proximal end of sheath 11 for attachment to hold end section 22 in position within sheath 11. The end cap has a central opening 36 through which rod 21 and light fibers 14 extend. The end cap can be rotated so that each tab 34 is displaced from its respective slot 32 into a peripheral groove 38 formed in the end cap. Light fibers 14, after they exit end cap 30, are bundled into a cable 40 which connects to a light source 42, shown in FIG. 1. It will be noted, that light fibers 14 and rod 21 both may exit through an opening in the cap enclosure 30. Although the drawing is done to show both detail on light fibers and electronic cable, it will be appreciated by those familiar with the technology that these cables actually exit through a water tight plastic strain relief to seal the system against water entry and to provide longer life to the two cables, i.e., light and electronic.

Conveniently, adjacent the proximate end of sheath 11 is a plastic cover 44 which is formed into an accordion shape and is connected to sheath 11, as by a ring 46. The cover 44 can be extended along the cables by pulling on pull tab 48 to pull cover 44 back over end cap 30 and down along cables 18 and 40.

It will be understood that core 15 may have been sterilized or disinfected by soaking or other means which do not require extremely high temperatures, so as not to damage the electronics. However, these methods are not always one-hundred percent effective and require long periods of time to accomplish. Just prior to use, the endoscope will be inserted into sterile sheath 11, as previously described, and cover 44 will be pulled down along cables 18 and 40. Thus, the entire portion of the endoscope inserted in the patient or associated with the patient will be completely sterile. After use, sheath 11 will be removed and thrown away and a new sterile sheath will be used for the next operative procedure.

The distal end of sheath 11 can be modified, as shown in FIG. 5, to have internal threads 50 for receiving a threaded lens assembly 52 whereby the internal threads 50 provide a point of attachment which is delimited by the circumference of elongated cylindrical core housing 15. This lens assembly can be constructed to allow straight ahead viewing with various fields of view, but it can also be made to allow angled viewing at 30°, 45°, 70° or any desired angle. This terminal lens assembly may also be an optical filter, which may also be removable. Alternatively, the lens assembly can be any desired combinatgion of viewing lenses and/or filters. The lens assembly can be made of material which enables it to be heat sterilized in an autoclave or the like.

Although not illustrated in FIG. 5, it will be understood that a window 12 may be used in conjunction with lens assembly 52 so that the distal end of the sheath is properly sealed. In such a case, the window 12 can be placed more within the sheath with the lens assembly 52 being positioned distally thereof, or the lens assembly 52 can be placed more within the sheath so that the window 12 is positioned distally thereof. Alternatively, as shown in FIG. 5, the positioning of threads 50 and lens assembly 52 can serve to properly seal the distal end of the sheath without the use of a window.

An alternative embodiment is shown in FIGS. 8–10 wherein the endoscope has a throwaway sheath 60 which is provided with a distal flexible tubular portion 62 and a proximal rigid cylindrical channel section 64 connected together as shown. Light fibers 14 and window 12 are attached to sheath 60, and are thrown away with sheath 60 after use. As in the previous embodiment, a cover 66 is provided which is in accordion configuration and has a pull tab 68 for pulling it down over the cables of the device. Sheath 60 is provided with a pair of steering wires 70 extending longitudinally through the wall of tubular section 62, as shown in FIG. 10, to a control 72 in cylindrical section 64, which works in a conventional manner for pushing or pulling the respective wires 70 to articulate the distal end of tubular section 62. If desired, a second pair of wires can be provided along with a second control for articulation in the opposite direction, all of which is well understood in the art. As in the previous embodiment, electronic housing 17 has a rod 21 extending from the proximal end thereof and through the opening in end cap 30. In this embodiment, the electronic housing 17 is received in the distal end of a core in the form of longitudinal tube 74 and the electronic wires extend longitudinally therethrough. It will be understood that this embodiment works just as the previous embodiment in respect to the placing the electronic housing with its associated tube 74 within the sheath 60 and holding it in position by means of end cap 30. Furthermore, it will be understood that, as in the previous embodiment, the image sensor 16 is slidably mounted within housing 17 with objective lens 19 hermetically sealed in the distal end of core 74. Additionally, as in the previous embodiment, the distal end of core 74 can be modified to include threaded lens assembly 52. The sheath is sterile before use and after use is disposed of and a new sterile sheath is used with the core 74 next time the endoscope is to be used on a patient.

A further alternative endoscope which has a sheath 80 is disclosed in FIGS. 11–13, wherein the sheath has a distal section 82 with operating channel passageways 84 extending longitudinally through the side walls. The distal cylindrical channel section 82 is formed integrally with a proximal section 86 having ports 88 in communication with passageways 84. This sheath is used when the light fibers for illumination are integral with the electronic housing. As best seen in FIG. 12, housing 17 is provided within a sleeve 90 having longitudinal light fibers 14 extending therethrough. This embodiment incorporates the same structure as the previous embodiments with respect to the image sensor 16, the housing 17, the lens 19, and the lens assembly 52 which may be added by modifying the core 74 in a similar fashion as shown in FIG. 5.

FIGS. 14–17 illustrate further embodiments which include sheath 150 which has a distal end section 152 and a proximal end section 154 which is larger than the distal portion and is integrally formed therewith, as shown. An accordion sleeve 156 is attached adjacent the proximal end of section 154 and has a pull tab 158 for pulling it down along a light cable 160. Conveniently, the distal end of light cable 160 is connected to the proximal end of section 154 and communicates with light fiber channel 161, as best seen in FIG. 15. Additionally, section 154 has one or more inlet ports, such as inlet ports 162 which communicate with irrigation channels 164, shown in FIG. 15. The sheath 150 is adapted to receive either of the core members shown in FIGS. 16 and 17. Core 166, shown in FIG. 16, has an objective lens 168, an image sensor 170 and a rod 172 connected in series as shown. The proximal end of rod 172 is connected to a locking mechanism 174 which is receivable and can be securely locked within the proximal end of section 154 of sheath 150.

Similarly, core member 176, as shown in FIG. 17 has a rod lens 178 connected at its proximal end to a camera 180 by means of a coupler 182. A locking mechanism 184 is connected between rod lens 176 and coupler 182 and is identical to locking mechanism 174 for locking into the proximal end of section 154 of sheath 150. Thus, it can be seen that cores 166 and 176 are interchangeable for use with the same sheath.

It will be understood that the embodiments in FIGS. 14–17 incorporate the same structural features as the previous embodiments with reference to a slidable Image sensor 168, an objective lens (not shown), and a threaded lens assembly 52 which may be added by modifying the respective core members 166 and 176 or sheath 150.

In yet another embodiment, as illustrated in FIGS. 18–21, an endoscope 200 is shown which is adapted to receive a transducer 230 through longitudinal tube or core 210 after an image of the surgical area has taken place by the imaging structure in housing 212. More specifically, FIG. 18 illustrates the endoscope 200 of this embodiment as having structure very similar to the embodiment of FIGS. 8 and 9 except that the distal end of the sheath/core combination may be left open by eliminating a distal window or cap. As shown, endoscope 200 includes a sheath 202 having a flexible distal part 204 and a more rigid proximal part 206. Sheath 202 encloses therein longitudinal tube or core 210 having a passageway 211 which is adapted to receive first the housing 212 and the transducer assembly 230 thereafter. As with the embodiment shown in FIGS. 8 and 9, this embodiment too may include a plurality of channels 208 formed through sheath 202 which have inserted therethrough a plurality of light fibers 209 in order to provide light to the surgical area. Alternatively, one or more of the channels 208 could receive a special small diameter instrument such as biopsy forceps, or the channels 208 could be used as passageways to carry fluid or gas to the surgical area. A sterile cover 216 may be positioned at the proximal end of the endoscope 200 in order to isolate the electronic transmission means or housed within rod 214. Conveniently, the pull tab 218 may be grasped and then pulled over the trailing cables. End cap 220 attaches to the proximal portion of the endoscope in order to stabilize focusing member 222 which moves the housing 212 along longitudinal tube or core 210. Additionally, a plurality of steering wires 224 may be positioned between the flexible part 204 and the longitudinal tube or core 210 so as to steer the distal end of the endoscope manipulated by the surgeon. Control 242 formed on handle 244 is used to control the manipulation of the steering wires.

As shown in FIG. 20, the transducer assembly 230 is similar in shape to the housing 212. More particularly, transducer assembly 230 includes a transducing element 232 located at the very distal end thereof, and another transducing element 234 arranged perpendicularly to element 232. Elements 232 and 234 attach to housing 236. Cable 238 extends proximally of the housing 236 and communicates with ultrasound equipment (not shown). The transducer assembly 230 is similar to units made commercially available for purposes of endoscopic ultrasonography.

One example of a commercially available transducer assembly which can be inserted within tube or core 210 and can provide a 360° radial image are two high frequency catheters with mechanically rotating transducers manufactured by Olympus America, Inc. of Melville, N.Y. and sold as components of the Olympus Ultrasonic Probe Set MH-247. Specifically, the catheter type transducers are sold as Model Nos. UM-24 (12 MHz) and UM-3R (20 MHz).

The ultrasonic endoscopy procedure is a high resolution imaging technique with applications that include staging of gastrointestinal malignancies, evaluation of gastrointestinal submucosal tumors, and diagnosis of diseases such as pancreaticobiliary disorders.

In operation, the surgeon utilizes the endoscope 200 to locate the area in which ultrasound imaging must take place. The housing 212 is then removed from within longitudinal tube or core 210 by removing the end cap 220, and transducer assembly 230 is then inserted through longitudinal tube or core 210. The transducer assembly 230 may protrude beyond the distal end of the sheath 202 in order to allow the assembly 230 to provide a desired image of the surgical area by the ultrasound technique.

One major advantage of providing a single instrument which can accommodate both a CCD or CMOS type imaging means and an ultrasound imaging means is that the surgical area which ultimately needs to be observed by the ultrasound transducer can be located more efficiently with minimal patient trauma. As well understood by those skilled in the art, an ultrasound transducer can best transmit ultrasound images of a surgical area when the transducer maintains continuous contact with a solid or liquid surface. Therefore, in those gastrointestinal procedures in which the transducer is placed through a duct or opening such as the esophagus which is not completely filled with a liquid, there can be a complete loss of the ultrasound image. Therefore, a photosensitive imaging means such as a CCD or CMOS type must initially be used to guide the endoscope to the area which is to be treated. By providing a removable core housing, once the surgical area to be later imaged by ultrasound is found by the photosensitive imaging element, it is simply removed while the endoscope remains in place and then the ultrasound transducer is introduced through the endoscope area. Since the endoscope is steerable, it can be precisely guided within a curved bodily passage minimizing trauma to the patient. Also, since the CCD/CMOS image sensor and the ultrasound transducer sequentially occupy the same space, the endoscope can be kept a minimum size. Although it is well-known to use a trochar for providing an opening through which any number of instruments may pass to view an internal organ, standard trochars do not have the ability to be manipulated into curved body passages nor do they contain removable imaging means or light fibers to illuminate the surgical area. The distal end of the endoscope of this embodiment can be as small as 2 mm to 3 mm in diameter which enables it to be placed in even the smallest bodily passages.

This invention has been described in detail with reference to particular embodiments thereof, but it will be understood that various other modifications can be effected within the spirit and scope of this invention.

I claim:

1. A method of performing endoscopic ultrasonography comprising the steps of:

providing an endoscopic instrument having a core, a photosensitive image sensor received within the core for providing a visual image of a surgical area under investigation, an electronic transmission means connected to said image sensor and extending proximally therefrom for transmitting electronic signals from the image sensor to a remote image display, a cylindrical sheath for receiving and positioning the core therethrough, the sheath having a plurality of longitudinal channels integrally disposed within and around the circumference of the sheath and communicating with the distal end thereof, and light fibers extending through at least one of the longitudinal channels for transmitting light to the surgical area;

creating a first visual image of the surgical area under investigation by means of the photosensitive image sensor;

removing the image sensor from within the core;

inserting an ultrasound transducer through the core;

positioning the transducer beyond the distal end of the sheath; and creating a second visual image of the surgical area under investigation by means of the ultrasound transducer.

2. A method, as claimed in claim 1, further including the step of:

introducing fluid through at least one of the longitudinal channels when the ultrasound transducer is imaging the surgical area under investigation.

3. A method, as claimed in claim 1, further including the step of:

steering the endoscope through the bodily passages of a patient prior to said positioning step in order to move the distal end of the sheath to a location adjacent the surgical area under investigation.

4. An endoscopic ultrasonography assembly comprising:

a cylindrical core having a distal end, a proximal end and a passageway extending longitudinally therethrough;

an image sensor slidably received into said proximal end of said cylindrical core and positionable through said passageway and adjacent said distal end thereof;

electronic transmission means having a distal end connected to said image sensor and having a proximal end extending proximally through said cylindrical core for transmitting electronic signals from said image sensor to a video device;

a cylindrical channel section having a distal end, a proximal end, and a central passageway for receiving said cylindrical core, said cylindrical channel section further including a plurality of longitudinal channels integrally disposed within and around the circumference of said cylindrical channel section, said longitudinal channels communicating with said distal end of said cylindrical channel section;

at least one light fiber extending through one of said longitudinal channels and extending to said distal end of said cylindrical channel section, said at least one light fiber used to illuminate a surgical site under investigation; and an ultrasound transducer insertable through said passageway of said core after said image sensor is removed.

5. An assembly, as claimed in claim 4, further including:

an operative instrument insertable through one of said longitudinal channels and protruding distally beyond said distal end of said cylindrical channel section in order to perform a desired surgical activity at the surgical site under investigation.

6. An assembly, as claimed in claim 4, further including:

fluid introduced through one of said longitudinal channels and delivered to the site under investigation.

7. An assembly, as claimed in claim 4, further including:

a plurality of steering wires insertable through corresponding longitudinal channels for providing a means to manipulate the distal end of the cylindrical channel section.

* * * * *

UNITED STATES PATENT AND TRADEMARK OFFICE
CERTIFICATE OF CORRECTION

PATENT NO. : 5,817,015
DATED : October 6, 1998
INVENTOR(S) : Edwin L. Adair

It is certified that error appears in the above-indentified patent and that said Letters Patent is hereby corrected as shown below:

On the first page, item [63], line 3, after "No." second occurrence, delete "5,402,323" and insert --5,402,768--.

Signed and Sealed this

Twenty-ninth Day of May, 2001

Attest:

NICHOLAS P. GODICI

Attesting Officer      Acting Director of the United States Patent and Trademark Office